(12) United States Patent
Tat et al.

(10) Patent No.: US 8,332,165 B1
(45) Date of Patent: Dec. 11, 2012

(54) ANALYSIS OF ULTRASONIC IMAGES USING A DECOMPOSITION PROCESS (75) Inventors: Hong Hue Tat, Redmond, WA (US); Yuan-Jye Wu, Issaquah, WA (US); Richard Henry Bossi, Renton, WA (US)

(73) Assignee: The Boeing Company, Chicago, IL (US)

( * ) Notice: Subject to any disclaimer, the term of this patent is extended or adjusted under 35 U.S.C. 154(b) by 273 days.

(21) Appl. No.: 12/877,340

(22) Filed: Sep. 8, 2010

(51) Int. Cl.
 *G01N 29/04* (2006.01)
(52) U.S. Cl. .......................................... 702/39
(58) Field of Classification Search ...................... 702/39
 See application file for complete search history.

(56) References Cited

OTHER PUBLICATIONS

David A Helweg, Using a binaural biomimetic array to identify bottom objects ensonified by echolocating dolphins, Aug. 17, 2006, IOP Publishing Ltd Printed in the UK, p. 41-51.*
Chen et al., "Nonnegativity constraints in numerical analysis", Proceedings Symposium on the Birth of Numerical Analysis, Leuven Belgium, Oct. 2007, pp. 1-31.
Berry et al., "Algorithms and Applications for Approximate Nonnegative Matrix Factorization", Computational Statistics and Data Analysis 52, 2007, pp. 155-173.
Gillis et al., "Dimensionality Reduction, Classification, and Spectral Mixture Analysis using Nonnegative Underapproximation", Proc. SPIE, vol. 7695, 76951A (2010); pp. 1-13.
Smith et al., "Automated Analysis and advanced Defect Characterisation from Ultrasonic Scans of Composites", Insight—Journal of the British Institute of NDT, vol. 51(2), pp. 82-87, 2009.
Bossi et al., "Wrinkle Detection and Measurement", Oct. 2007, CAGE Code 81205, ECCN EAR 99, Physics (9MPW-E010), Boeing, pp. 1-42.

* cited by examiner

*Primary Examiner* — Tung S Lau
(74) *Attorney, Agent, or Firm* — Yee & Associates, P.C.

(57) ABSTRACT

A method and apparatus for identifying features for an object. Response signals are received in response to sending signals into an object at locations using a measurement system. A first matrix is formed. Each entry in the first matrix contains an amplitude of a response signal for a location and time at which the response signal was received with respect to when a corresponding signal was sent into the object. The first matrix is decomposed into a second matrix and third matrix such that a product of the second and third matrices represents the first matrix. A number of columns in the second matrix corresponds to a number of features for the object. A number of rows in the third matrix corresponds to a number of sets of weighting factors for the number of features. Information is identified about the features in the object using the second and third matrices.

22 Claims, 8 Drawing Sheets

ANALYSIS OF ULTRASONIC IMAGES USING A DECOMPOSITION PROCESS

BACKGROUND INFORMATION

1. Field

The present disclosure relates generally to testing components and, in particular, to testing composite components for inconsistencies. Still more particularly, the present disclosure provides a method and apparatus for identifying wrinkles in composite components.

2. Background

Aircraft are being designed and manufactured with greater and greater percentages of composite materials. Some aircraft may have more than 50 percent of their primary structure made from composite materials. Composite materials are used in aircraft to decrease the weight of the aircraft. This decreased weight improves performance features, such as payload capacities and fuel efficiencies. Further, composite materials provide longer service life for various components in an aircraft.

Composite materials are tough, light-weight materials created by combining two or more dissimilar components. For example, a composite may include fibers and resins. The fibers may be in the form of a substrate or matrix. For example, the fibers may take the form of a woven cloth. The resin may form a reinforcement for the substrate. The fibers and resins are combined and cured to form a composite material.

Composite materials are used in components, such as, for example, without limitation, support beams, frames, and stiffeners for aircraft or other vehicles in which reduced weight, increased strength, and improved corrosion and fatigue resistance is desired. Such components may be formed by laying up plies of composite materials to form a structure for the desired components and then cured with a resin infused in the layers of plies. The plies may be, for example, unidirectional carbon fiber composite materials.

Inconsistencies may occur during the manufacturing of the components. For example, some of the plies may wrinkle during the fabrication of certain components. In particular, components having a curved configuration or having non-uniform cross sections along the length of the component may have wrinkles. Such wrinkles are often undesirable, because the wrinkles may result in a reduction in performance of the component.

Ultrasonic signals have been used to identify inconsistencies in composite components. For example, pulse echo (PE) and through transmission ultrasonic (TTU) methods are currently used to detect wrinkles in composite components. X-rays also have been used to detect inconsistencies in composite components. X-rays are sensitive to changes in the composite laminate caused by inconsistencies, such as wrinkles.

The identification of a wrinkle includes more than detecting the presence of a wrinkle. The presence of a wrinkle may not affect the performance of the component such that reworking or replacement of the component is needed. The dimensions of the wrinkle are used to determine whether actions are to be taken.

As a result in nondestructive testing of components, the identification also may include measuring dimensions for the wrinkle. Ultrasonic nondestructive evaluation procedures can be sensitive enough to identify dimensions of plies in composite laminates if the frequency is sufficiently high.

In the case where a wrinkle is detected but cannot be measured, the component may be reworked or discarded. This result may occur even if the wrinkle does not affect the performance of the component. The inability to measure the dimensions of the wrinkle, however, may result in increased costs and time to rework the component or to manufacture another component as a replacement.

Therefore, it would be advantageous to have an apparatus and method that takes into account one or more of the issues discussed above, as well as possibly other issues.

SUMMARY

In one advantageous embodiment, a method is provided for identifying features in an object. Signals are sent into the object at a plurality of locations using a measurement system. Response signals are received using the measurement system in response to sending the signals into the object at the plurality of locations. A first matrix is formed in which each entry in the first matrix contains an amplitude of a response signal in the response signals for a location in the plurality of locations where the response signal was received and for a time at which the response signal was received with respect to when a corresponding signal in the signals was sent into the object. The first matrix is decomposed into a second matrix and a third matrix such that a product of the second matrix and the third matrix represents the first matrix. A number of columns in the second matrix corresponds to a number of features for the object. A number of rows in the third matrix corresponds to a number of sets of weighting factors for the number of features. Information is identified about the features in the object using the second matrix and the third matrix.

In another advantageous embodiment, an apparatus comprises a measurement system and a computer system. The measurement system is configured to send signals into an object at a plurality of locations and receive response signals in response to sending the signals into the object at the plurality of locations. The computer system is configured to form a first matrix. Each entry in the first matrix contains an amplitude of a response signal in the response signals for a location in the plurality of locations where the response signal was received and a time at which the response signal was received with respect to when a corresponding signal in the signals was sent into the object. The computers system is configured to decompose the first matrix into a second matrix and a third matrix such that a product of the second matrix and the third matrix represents the first matrix. A number of columns in the second matrix corresponds to a number of features for the object. A number of rows in the third matrix corresponds to a number of sets of weighting factors for the number of features. The computer system is configured to identify information about the features in the object using the second matrix and the third matrix.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives, and advantages thereof, will best be understood by reference to the following detailed description of an advantageous embodiment of the present disclosure when read in conjunction with the accompanying drawings, wherein:

DETAILED DESCRIPTION

Figure 1:
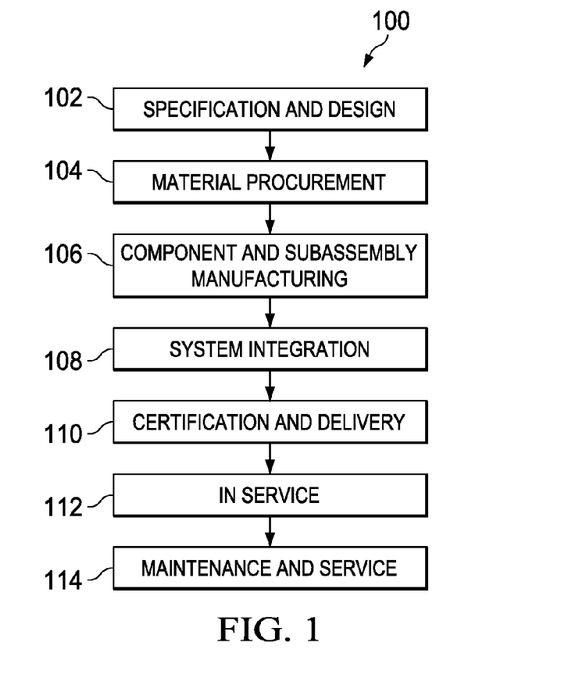
FIG. 1 is an illustration of an aircraft manufacturing and service method in accordance with an advantageous embodiment.
Figure 2:
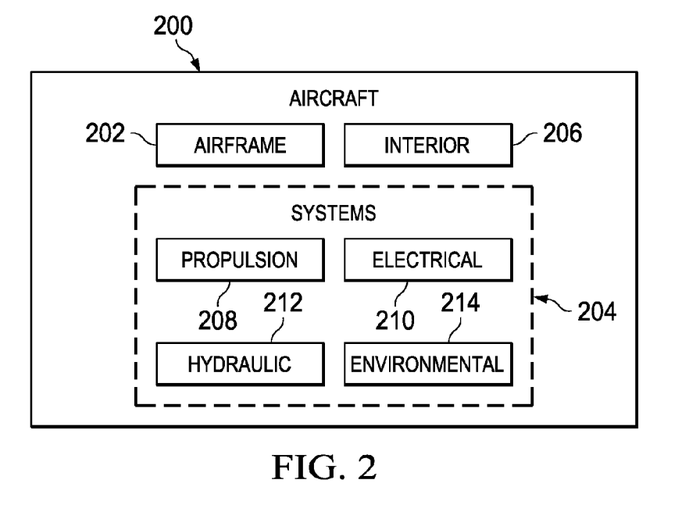
FIG. 2 is an illustration of an aircraft in which an advantageous embodiment may be implemented.

Referring more particularly to the drawings, embodiments of the disclosure may be described in the context of aircraft manufacturing and service method 100 as shown in FIG. 1 and aircraft 200 as shown in FIG. 2. Turning first to FIG. 1, an illustration of an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service 112 by a customer, aircraft 200 in FIG. 2 is scheduled for routine maintenance and service 114, which may include modification, reconfiguration, refurbishment, and other maintenance service.

Each of the processes of aircraft manufacturing and service method 100 may be performed or carried out by a system integrator, a third party, and/or an operator. In these examples, the operator may be a customer. For the purpose of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

With reference now to FIG. 2, an illustration of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion systems 208, electrical system 210, hydraulic system 212, and environmental system 214. Any number of other systems may be included. Although an aerospace example is shown, different advantageous embodiments may be applied to other industries, such as the automotive industry.

The apparatus and methods embodied herein may be employed during at least one of the stages of aircraft manufacturing and service method 100 in FIG. 1. As used herein, the phrase "at least one of", when used with a list of items, means that different combinations of one or more of the listed items may be used and only one of each item in the list may be needed. For example, "at least one of item A, item B, and item C" may include, for example and without limitation, item A or item A and item B. This example also may include item A, item B, and item C or item B and item C.

As one illustrative example, components or subassemblies produced in component and subassembly manufacturing 106 in FIG. 1 may be fabricated or manufactured in a manner similar to components or subassemblies produced while aircraft 200 is in service 112 in FIG. 1. As yet another example, a number of apparatus embodiments, method embodiments, or a combination thereof may be utilized during production stages, such as component and subassembly manufacturing 106 and system integration 108 in FIG. 1.

The different advantageous embodiments recognize and take into account a number of considerations. For example, the different advantageous embodiments recognize and take into account that tape or fabric formed with resin may be laid up and put in a mold under heat and pressure. When the heat is removed, the resin matrix material solidifies and can be formed into various shapes. A feature of composite materials is that composite materials can be layered, with the fibers in each layer running in a different direction. This configuration allows the components to be designed to behave in certain ways.

The different advantageous embodiments recognize and take into account, however, that some of the plies may wrinkle during the fabrication of certain composite components. These composite components may include, for example, components having a curved configuration or components having non-uniform cross sections along the length of the component. Such wrinkles are often undesirable as they may result in a reduction in performance of the component.

A nondestructive evaluation (NDE) technique may be used to detect and measure wrinkles to ensure that the wrinkles have sizes that meet selected criteria. The criteria for the wrinkles may be selected using any suitable criteria for wrinkles.

For example, the different advantageous embodiments recognize and take into account that signals from a measurement system may be sent into an object formed from layers of composite materials. Response signals are received in response to sending the signals. These response signals may be used to form an image that provides a view of time versus distance. The time correlates to depth in the component.

Thus, the different advantageous embodiments provide a method and apparatus for identifying features in an object. In one advantageous embodiment, signals are sent into the object at a plurality of locations using a measurement system. Response signals are received at the plurality of locations in response to sending the signals. A first matrix is formed in which each entry in the first matrix contains an amplitude of a response signal in the response signals for a location in the plurality of locations where the response signal was received and for a time at which the response signal was received with respect to when a corresponding signal in the signals was sent into the object.

The first matrix is decomposed into a second matrix and a third matrix such that a product of the second matrix and the third matrix represents the first matrix. A number of columns in the second matrix corresponds to a number of features for the object. A number of rows in the third matrix corresponds to a number of sets of weighting factors for the number of features. Information is identified about the features in the object using the second matrix and the third matrix.

Figure 3:
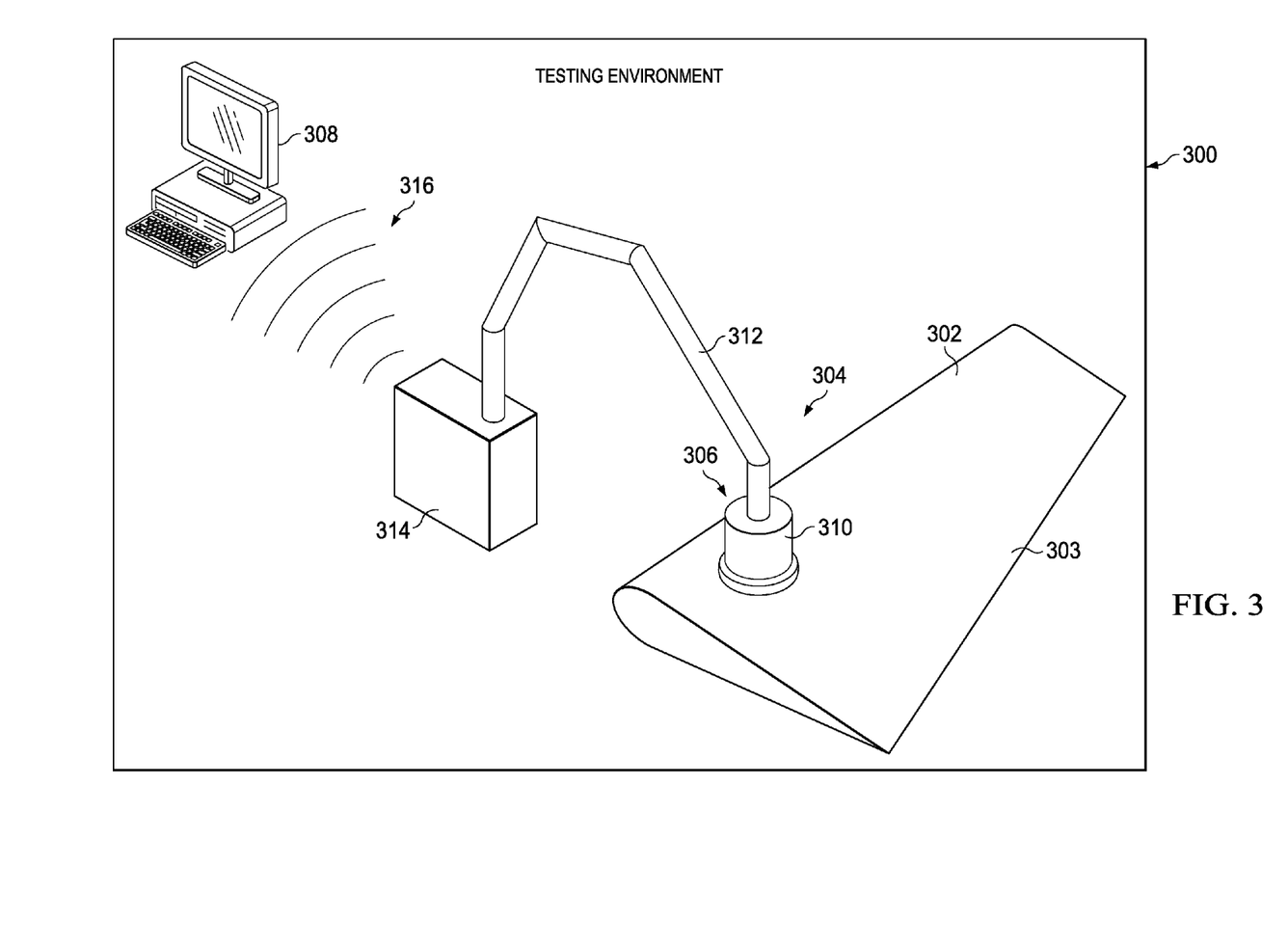
FIG. 3 is an illustration of a testing environment in accordance with an advantageous embodiment.

With reference now to FIG. 3, an illustration of a testing environment is depicted in accordance with an advantageous embodiment. In this illustrative example, testing environment 300 is an environment for testing object 302. Object 302 is wing 303. Wing 303 may be for an aircraft, such as aircraft 200 in FIG. 2. Wing 303 is comprised of composite materials in this example.

As one illustrative example, wing 303 may be tested during aircraft manufacturing and service method 100 in FIG. 1. For example, object 302 may be tested during component and subassembly manufacturing 106, system integration 108, certification and delivery 110, in service 112, and/or routine maintenance and service 114 in FIG. 1.

In this illustrative example, wing 303 is tested using testing system 304. Testing system 304 includes ultrasonic measurement system 306 and computer system 308. Computer system 308 is located remote to ultrasonic measurement system 306 in this depicted example. Ultrasonic measurement system 306 includes probe 310, arm 312, and robotic machine 314. Probe 310 is connected to robotic machine 314 using arm 312. Robotic machine 314 and arm 312 allow probe 310 to be moved to various locations on wing 303.

Ultrasonic measurement system 306 is configured to send ultrasonic signals into wing 303 and receive response signals in response to the ultrasonic signals. Further, ultrasonic measurement system 306 is configured to send the response signals received to computer system 308. More specifically, ultrasonic measurement system 306 sends information about the response signals to computer system 308 using wireless communication link 316. Of course, in other illustrative examples, information may be sent to computer system 308 using a wired communications link.

Computer system 308 is configured to use this information to identify inconsistencies in wing 303. Additionally, computer system 308 may be configured to identify information about the inconsistencies, such as locations of the inconsistencies, characteristics of the inconsistencies, dimensions for the inconsistencies, and/or other suitable types of information.

Inconsistencies in wing 303 may include, for example, without limitation, a wrinkle in the layers of composite materials forming wing 303, a separation of the layers of composite materials, and/or other suitable types of inconsistencies.

Figure 4:
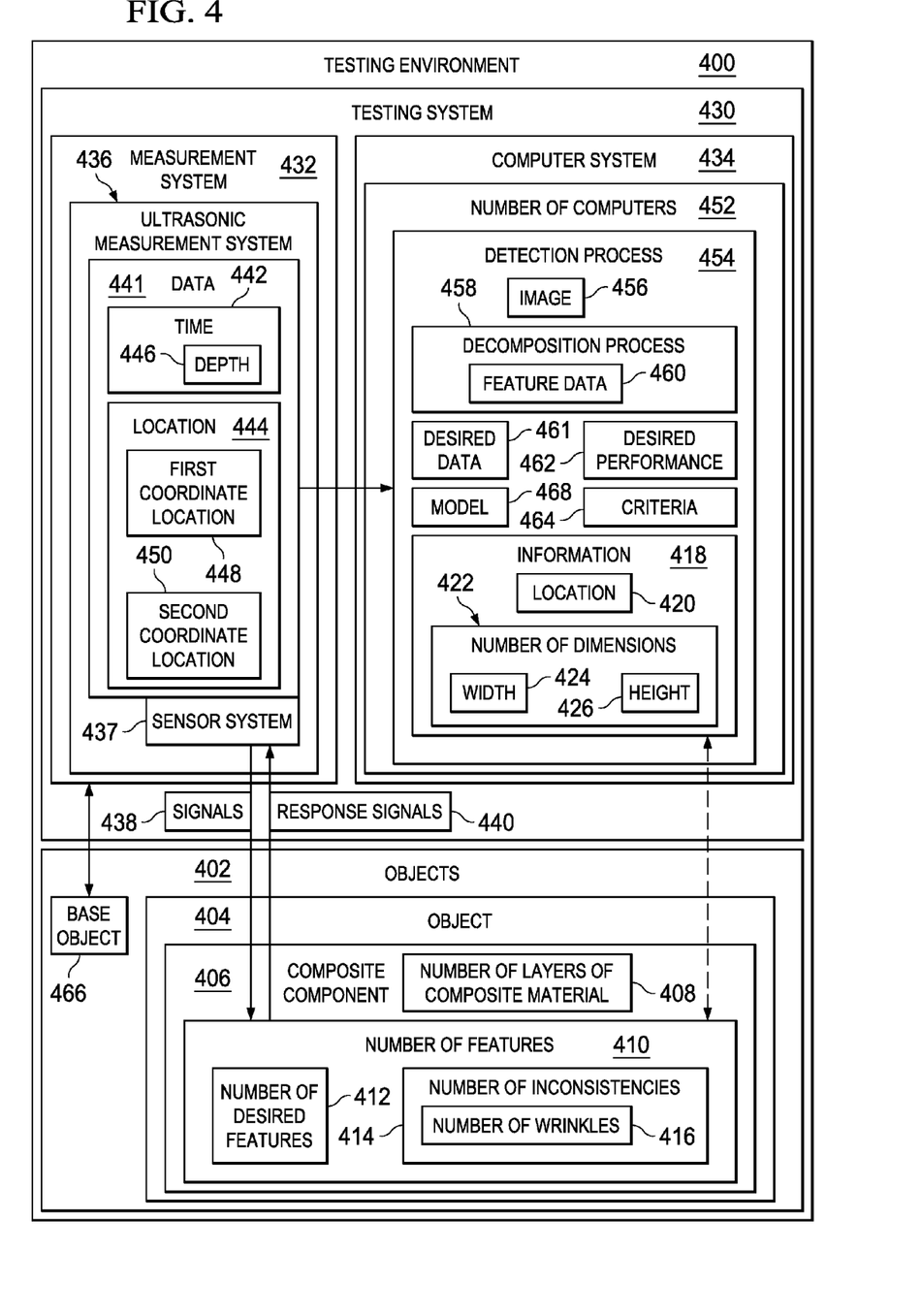
FIG. 4 is an illustration of a testing environment in accordance with an advantageous embodiment.

With reference now to FIG. 4, an illustration of a testing environment is depicted in accordance with an advantageous embodiment. Testing environment 300 in FIG. 3 is an example of one implementation for testing environment 400 in FIG. 4. In this illustrative example, testing environment 400 is an example of an environment that may be used to test objects 402.

Objects 402 may be components, parts, structures, or other objects in a platform, such as aircraft 200 in FIG. 2. In these illustrative examples, object 404 is composite component 406. For example, composite component 406 is comprised of number of layers of composite material 408. A number, as used herein with reference to an item, means one or more items. For example, number of layers of composite material 408 is one or more layers of composite material.

In forming composite component 406, number of layers of composite material 408 may be formed in a number of different ways. As one illustrative example, number of layers of composite material 408 may be laid up on top of each other and then cured to form composite component 406. Each of number of layers of composite material 408 may be laid up in a same or different direction as the other layers of composite material. The curing of number of layers of composite material 408 may be performed using, for example, an oven, an autoclave, or some other suitable type of heating process.

During the forming of composite component 406, composite component 406 may be formed with number of features 410. As one illustrative example, number of features 410 may be formed in composite component 406 during the curing of number of layers of composite material 408.

Number of features 410 may include number of desired features 412 and number of inconsistencies 414. Number of desired features 412 may include, for example, without limitation, number of layers of composite material 408 being substantially parallel to a plane. In this manner, number of layers of composite material 408 may be substantially parallel to each other in the portions of composite component 406 with number of desired features 412.

Number of inconsistencies 414 includes undesired features in these examples. Number of inconsistencies 414 may be selected from at least one of number of layers of composite material 408 not being substantially parallel to a plane, a number of wrinkles in number of layers of composite material 408, a number of voids in a region of number of layers of composite material 408, and/or other suitable types of inconsistencies.

In these illustrative examples, number of inconsistencies 414 takes the form of number of wrinkles 416. A wrinkle is a presence of a change in number of layers of composite material 408 such that number of layers of composite material 408 is not substantially parallel to each other.

In the different advantageous embodiments, it is desirable to obtain information 418 about number of features 410 for composite component 406. Information 418 may include, for example, location 420, number of dimensions 422, and/or other suitable types of information for a feature in number of features 410. For example, location 420 for an inconsistency in number of inconsistencies 414 is a location in composite component 406 for the inconsistency. Number of dimensions 422 for an inconsistency may include, for example, without limitation, width 424, height 426, and/or other dimensions for the inconsistency.

In these illustrative examples, information 418 about number of features 410 is obtained using testing system 430. Testing system 430 includes measurement system 432 and computer system 434. Measurement system 432 takes the form of ultrasonic measurement system 436 in this example. Ultrasonic measurement system 436 is configured to send signals 438 into composite component 406. Further, ultrasonic measurement system 436 is configured to receive response signals 440 in response to signals 438 being sent into composite component 406.

In these depicted examples, the sending of signals 438 and the receiving of response signals 440 is performed using sensor system 437. Sensor system 437 may take a number of different forms. For example, sensor system 437 may be a transducer system, a laser system, or some other suitable type of system configured to send signals 438 and receive response signals 440.

The receiving of and any processing of response signals 440 by ultrasonic measurement system 436 forms data 441. Data 441 includes the recording of response signals 440 by ultrasonic measurement system 436 as time 442 versus location 444.

Time 442 represents depth 446 for composite component 406 in these examples. Location 444 is identified using a two-dimensional coordinate system in these examples. In particular, location 444 includes first coordinate location 448 and second coordinate location 450. First coordinate location

448 may be, for example, an x-coordinate location on composite component 406. Second coordinate location 450 may be, for example, a y-coordinate location on composite component 406.

In these illustrative examples, ultrasonic measurement system 436 sends data 441 to computer system 434. Data 441 may be sent to computer system 434 using a wired communications link and/or a wireless communications link. Computer system 434 comprises number of computers 452. Detection process 454 runs on number of computers 452 in these illustrative examples. Detection process 454 may run as program code processed by number of computers 452. In some illustrative examples, all or a portion of detection process 454 may be embodied in hardware in number of computers 452.

Detection process 454 is configured to receive data 441 and generate image 456 for composite component 406. In these illustrative examples, image 456 is a B-scan image. A B-scan image presents the amount of ultrasonic energy received in response signals 440 with respect to time 442 and one of first coordinate location 448 and second coordinate location 450.

In these illustrative examples, detection process 454 uses data 441 and/or image 456 to perform decomposition process 458. Decomposition process 458 is used to identify information 418 about number of features 410 in composite component 406. For example, decomposition process 458 may be used to generate feature data 460 about number of features 410.

Feature data 460 is data generated by comparing data 441 for composite component 406 with desired data 461. Desired data 461 is data for a composite component in which undesired inconsistencies are absent. In other words, desired data 461 is for a composite component in which the number of layers of composite material for the composite component is substantially parallel to a plane. Further, desired data 461 is for a composite component in which substantially the entire composite component has number of desired features 412.

In these illustrative examples, desired data 461 may be derived from a number of different sources. For example, desired data 461 may be derived from testing base object 466 using ultrasonic measurement system 436. Base object 466 is a version of object 404 for which desired data 461 is generated when tested with ultrasonic measurement system 436.

In some illustrative examples, desired data 461 may be derived from model 468 of object 404. Model 468, in this example, is a computer-aided design model or some other electronic file containing information about desired data 461. Of course, in other illustrative examples, desired data 461 may be derived in some other suitable manner.

In these illustrative examples, feature data 460 may be used to identify information 418, such as width 424, for features in number of features 410 in composite component 406. For example, feature data 460 may be used to identify width 424 for a wrinkle in number of wrinkles 416.

Depending on the value for width 424 for number of inconsistencies 414 in composite component 406, composite component 406 may not have desired performance 462. If composite component 406 does not have desired performance 462, composite component 406 may be reworked or discarded in some illustrative examples. For example, if width 424 for a wrinkle in number of wrinkles 416 does not meet criteria 464, composite component 406 may need to be reworked to decrease width 424 for the wrinkle and/or remove the wrinkle.

In this manner, information 418 obtained using detection process 454 may be used to determine what actions, if any, need to be taken for composite component 406.

Figure 5:
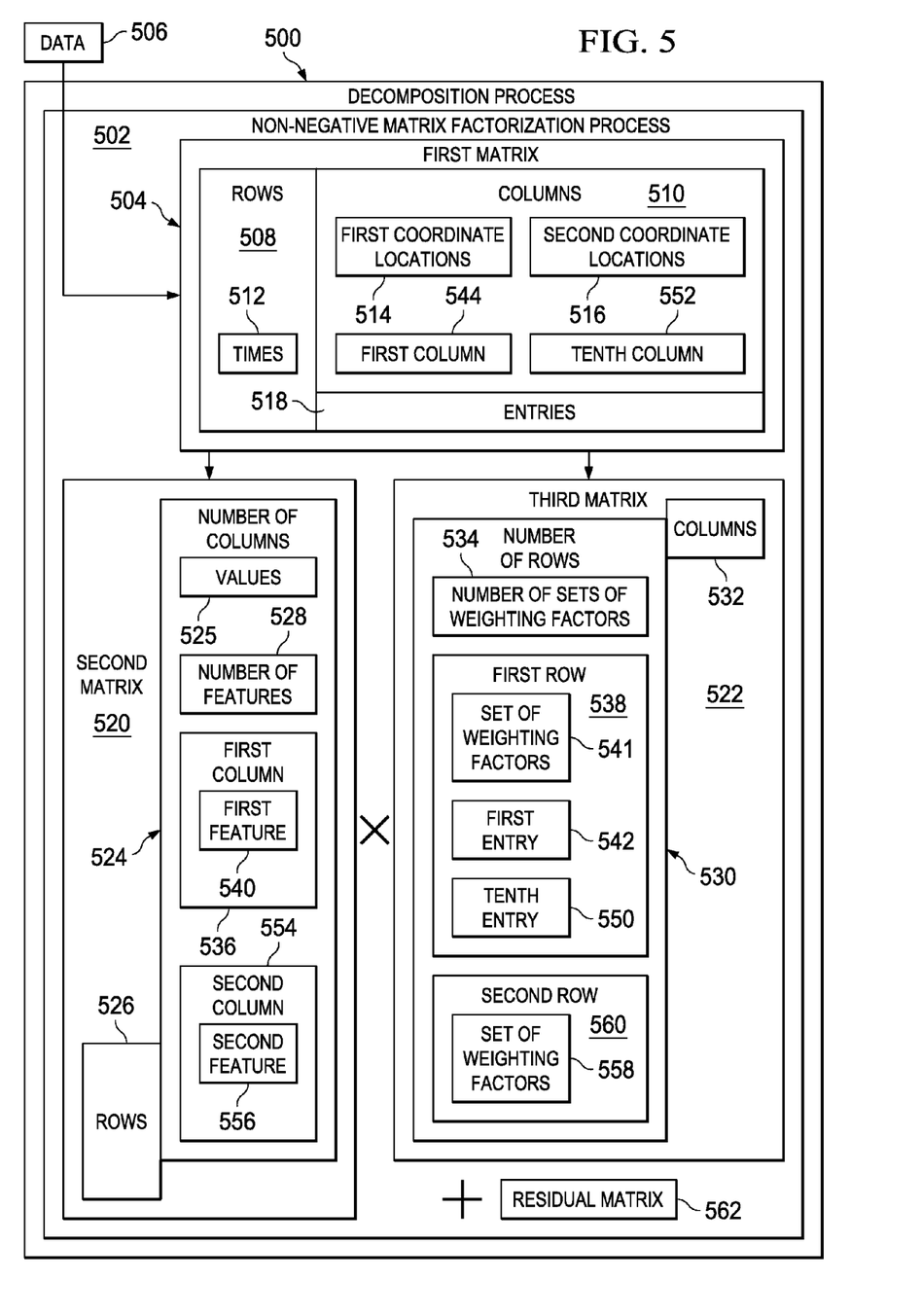
FIG. 5 is an illustration of a block diagram of a decomposition process in accordance with an advantageous embodiment.

With reference now to FIG. 5, an illustration of a block diagram of a decomposition process is depicted in accordance with an advantageous embodiment. In this illustrative example, decomposition process 500 is an example of one implementation for decomposition process 458 in FIG. 4. Decomposition process 500 takes the form of non-negative matrix factorization process 502 in this illustrative example.

As depicted, decomposition process 500 forms first matrix 504 using data 506. Data 506 is data that has been generated for an object, such as composite component 406 in FIG. 4, using an ultrasonic measurement system, such as ultrasonic measurement system 436 in FIG. 4. For example, data 506 is data 441 in FIG. 4.

First matrix 504 has rows 508 and columns 510. Rows 508 are for times 512. Times 512 are the times at which response signals, such as response signals 440 in FIG. 4, were received by the ultrasonic measurement system with respect to when signals, such as signals 438 in FIG. 4, were sent into the composite component. Times 512 correspond to a depth for the composite component.

Columns 510 are for locations for the composite component at which signals were sent into the composite component and for which response signals were received. In particular, columns 510 are for one of first coordinate locations 514 and second coordinate locations 516. In these illustrative examples, first coordinate locations 514 are x-coordinate locations. Second coordinate locations 516 are y-coordinate locations. These x-coordinate locations and y-coordinate locations are locations on the composite component.

Columns 510 are for first coordinate locations 514 when first matrix 504 is formed for a particular second coordinate location. Similarly, columns 510 are for second coordinate locations 516 when first matrix 504 is formed for a particular first coordinate location.

Each entry in entries 518 for first matrix 504 contains an amplitude of the response signal with respect to the time and location for which the response signal was received. Further, entries 518 contain values for the data that may be presented in an image, such as image 456 in FIG. 4.

In this illustrative example, decomposition process 500 decomposes first matrix 504 into second matrix 520 and third matrix 522 such that a product of second matrix 520 and third matrix 522 is a representation of first matrix 504. This representation of first matrix 504 may be referred to as an approximation of first matrix 504. The entries for each of first matrix 504, second matrix 520, and third matrix 522 contain non-negative values in this depicted example.

Second matrix 520 has number of columns 524 and rows 526. Number of columns 524 corresponds to number of features 528. In particular, each column in number of columns 524 corresponds to a feature in number of features 528.

Each column in number of columns 524 has values 525. Values 525 are the values for the feature corresponding to the particular column. These values may be the amplitudes of the response signals received and/or expected for the feature corresponding to the particular column. For example, values 525 may be selected using a model that provides the values expected for the particular feature. Values 525 may be selected by decomposition process 500 and/or a user.

Rows 526 for second matrix 520 correspond to rows 508 for first matrix 504. In other words, each row in rows 526 corresponds to a time in times 512.

Third matrix 522 has number of rows 530 and columns 532. Number of rows 530 is for number of sets of weighting factors 534. In particular, each row in number of rows 530 is for a set of weighting factors in number of sets of weighting factors 534 that corresponds to a particular column in number of columns 524. In this manner, each set of weighting factors in number of sets of weighting factors 534 corresponds to a feature in number of features 528.

Columns 532 for third matrix 522 correspond to columns 510 for first matrix 504. In other words, each column in columns 532 corresponds to a location in either first coordinate locations 514 or second coordinate locations 516 selected for columns 510 for first matrix 504.

In this illustrative example, first column 536 in number of columns 524 for second matrix 520 corresponds to first feature 540. In this illustrative example, first feature 540 is a number of layers of composite material for the composite component being substantially parallel to a plane. In other words, first feature 540 may be the number of layers of composite material being substantially parallel to each other. First feature 540 may be selected by a user and/or decomposition process 500.

First column 536 may be multiplied by first row 538 in number of rows 530 in third matrix 522 to represent first matrix 504 with respect to first feature 540 corresponding to first column 536. First row 538 contains set of weighting factors 541. Set of weighting factors 541 for first row 538 is the set of weighting factors in which the product of values 525 for first column 536 and set of weighting factors 541 is a representation of first matrix 504 with respect to first feature 540.

As one illustrative example, first column 536 may be multiplied by first entry 542 in first row 538 to represent first column 544 in columns 510 for first matrix 504 with respect to first feature 540. Similarly, first column 536 in number of columns 524 may be multiplied by the other entries in first row 538 to represent the other columns in columns 510 for first matrix 504 with respect to first feature 540.

The values for set of weighting factors 541 for first row 538 may be scaled between a range of zero and one in this illustrative example. An entry in first row 538 with a value closer to one indicates that the portion of the composite component at the location corresponding to the column in columns 510 of first matrix 504 that corresponds to the entry in first row 538 is more similar to first feature 540. A value of zero indicates that the portion of the composite component at the location corresponding to the column in columns 510 of first matrix 504 that corresponds to the entry in first row 538 is less similar to first feature 540.

Of course, in other illustrative examples, other ranges of weighting factors may be used. For example, in other illustrative examples, the values for set of weighting factors 541 for first row 538 may be scaled between a range of about zero and about 100.

The values for set of weighting factors 541 may be used to obtain information about the features in the composite component with respect to first feature 540. For example, the values may be used to identify inconsistencies in which portions of the composite component are different from first feature 540 outside of a selected range of values. In other words, a value for a weighting factor outside of a selected range of values may indicate that the corresponding portion of the composite component is an inconsistency with respect to first feature 540.

In this illustrative example, the value closest to zero in set of weighting factors 541 is used to identify an inconsistency in the composite component. As one illustrative example, this inconsistency may be identified at tenth entry 550 in first row 538. Tenth entry 550 in first row 538 corresponds to tenth column 552 in columns 510 for first matrix 504. Tenth column 552 corresponds to a particular location for the composite component at which the inconsistency is identified. The values for tenth column 552 may be used as the values for second column 554 in number of columns 524 for second matrix 520. In this manner, the inconsistency identified in tenth column 552 in first matrix 504 is used as second feature 556 in number of features 528 for second column 554.

Decomposition process 500 identifies set of weighting factors 558 for second row 560 in third matrix 522 based on second column 554 in second matrix 520. The product of second column 554 and second row 560 is a representation of first matrix 504 with respect to second feature 556. The values for set of weighting factors 558 for second row 560 may be used to identify the location and/or other information for the inconsistency. For example, a width of the inconsistency may be identified.

In this manner, the product of second matrix 520 with first column 536 and second column 554, and third matrix 522 with first row 538 and second row 560, represents first matrix 504. This representation of first matrix 504 using second matrix 520 and third matrix 522 is given by the equation as follows:

$$A \approx \begin{pmatrix} w_1 & w_2 \end{pmatrix} \cdot \begin{pmatrix} h_1 \\ h_2 \end{pmatrix} = w_1 \cdot h_1 + w_2 \cdot h_2,$$

where A is first matrix 504, $w_1$ is first column 536 in second matrix 520, $w_2$ is second column 554 in second matrix 520, $h_1$ is first row 538 in third matrix 522, and $h_2$ is second row 560 in third matrix 522.

As one illustrative example, first column 544 in first matrix 504 may be represented as follows:

$$a_1 \approx w_1 \cdot h_{11} + w_2 \cdot h_{21}$$

where $a_1$ is first column 544 for first matrix 504, $h_{11}$ is the first entry in first row 538 of third matrix 522, and $h_{21}$ is the first entry in second row 560 of third matrix 522. In this manner, first column 544 is represented with respect to first feature 540 as $w_1 \cdot h_{11}$. Further, first column 544 is represented with respect to second feature 556 as $w_2 \cdot h_{21}$.

In these illustrative examples, the product of second matrix 520 and third matrix 522 may be added with residual matrix 562 to equal first matrix 504. Residual matrix 562 has entries that contain non-negative and/or negative values in this example.

The illustrations of testing environment 400 in FIG. 4 and decomposition process 500 in FIG. 5 are not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, in some illustrative examples, measurement system 432 may take the form of a computerized tomography system. In other examples, measurement system 432 may send signals 438 having frequencies outside of the ultrasonic frequency range. As one illustrative example, measurement system 432 may send signals 438 having frequencies between about one megahertz and about 20 megahertz for ultrasound signals.

Additionally, in some illustrative examples, object 404 in FIG. 4 may not be a composite component. Object 404 may be a metal object, a nonmetal object, a reworked component, or some other suitable type of object. In other illustrative examples, ultrasonic measurement system 436 may be configured to generate image 456 and send image 456 to computer system 434. In some illustrative examples, computer system 434 may be part of ultrasonic measurement system 436.

Further, in other illustrative examples, testing system 430 may be used to test objects 402 for platforms other than aircraft. For example, objects 402 may be for a platform selected from one of a mobile platform, a stationary platform, a land-based structure, an aquatic-based structure, a space-based structure, an aircraft, a surface ship, a tank, a personnel carrier, a train, a spacecraft, a space station, a satellite, a submarine, an automobile, a power plant, a bridge, a dam, a manufacturing facility, and a building.

Additionally, in still other illustrative examples, rows 508 in first matrix 504 in FIG. 5 may be selected from one of first coordinate locations 514 and second coordinate locations 516, while columns 510 are for times 512. Similarly, rows 508 may be selected as first coordinate locations 514 or second coordinate locations 516, and columns 510 may be selected as second coordinate locations 516 or first coordinate locations, respectively.

Figure 6:
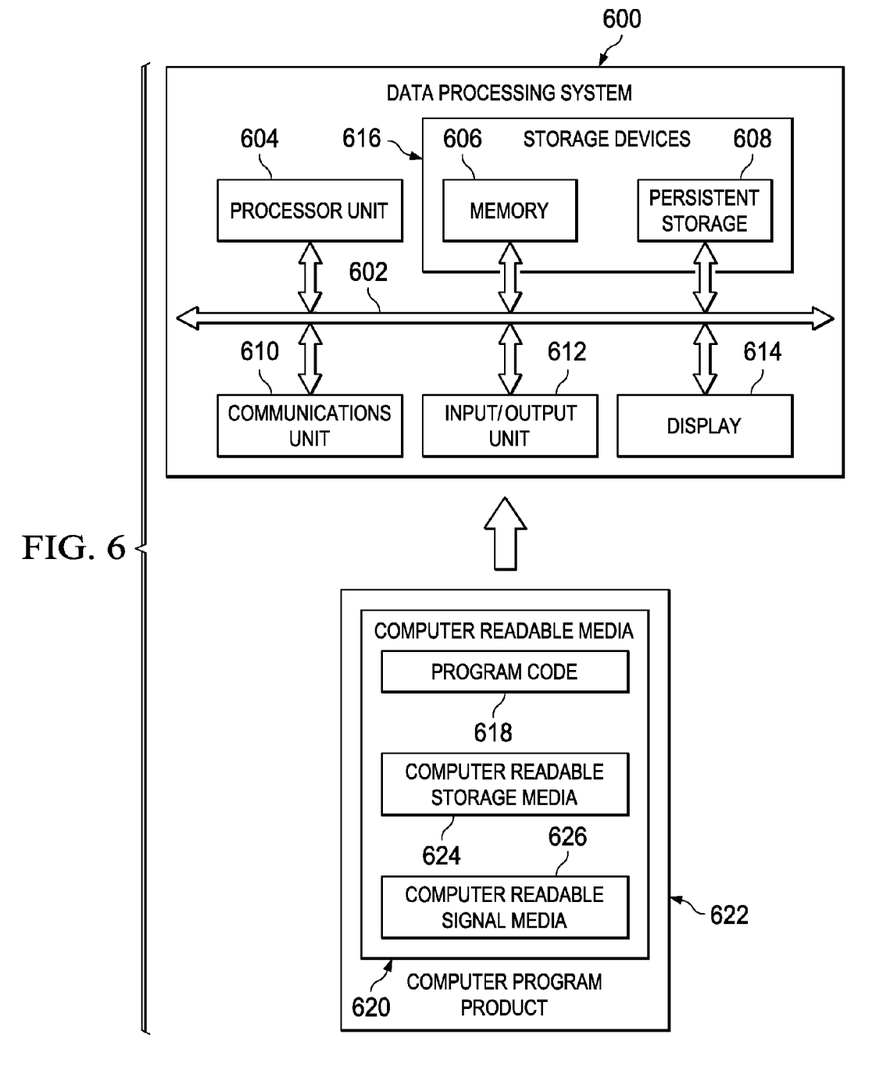
FIG. 6 is an illustration of a data processing system in accordance with an advantageous embodiment.

Turning now to FIG. 6, an illustration of a diagram of a data processing system is depicted in accordance with an advantageous embodiment. In this illustrative example, data processing system 600 includes communications fabric 602, which provides communications between processor unit 604, memory 606, persistent storage 608, communications unit 610, input/output (I/O) unit 612, and display 614.

Processor unit 604 serves to execute instructions for software that may be loaded into memory 606. Processor unit 604 may be a set of one or more processors or may be a multi-processor core, depending on the particular implementation. Further, processor unit 604 may be implemented using one or more heterogeneous processor systems, in which a main processor is present with secondary processors on a single chip. As another advantageous example, processor unit 604 may be a symmetric multi-processor system containing multiple processors of the same type.

Memory 606 and persistent storage 608 are examples of storage devices 616. A storage device is any piece of hardware that is capable of storing information, such as, for example, without limitation, data, program code in functional form, and/or other suitable information either on a temporary basis and/or a permanent basis. Storage devices 616 may also be referred to as computer readable storage devices in these examples. Memory 606, in these examples, may be, for example, a random access memory, or any other suitable volatile or non-volatile storage device.

Persistent storage 608 may take various forms, depending on the particular implementation. For example, persistent storage 608 may contain one or more components or devices. For example, persistent storage 608 may be a hard drive, a flash memory, a rewritable optical disk, a rewritable magnetic tape, or some combination of the above. The media used by persistent storage 608 may be removable. For example, a removable hard drive may be used for persistent storage 608.

Communications unit 610, in these examples, provides for communication with other data processing systems or devices. In these examples, communications unit 610 is a network interface card. Communications unit 610 may provide communications through the use of either or both physical and wireless communications links.

Input/output unit 612 allows for the input and output of data with other devices that may be connected to data processing system 600. For example, input/output unit 612 may provide a connection for user input through a keyboard, a mouse, and/or some other suitable input device. Further, input/output unit 612 may send output to a printer. Display 614 provides a mechanism to display information to a user.

Instructions for the operating system, applications, and/or programs may be located in storage devices 616, which are in communication with processor unit 604 through communications fabric 602. In these illustrative examples, the instructions are in a functional form on persistent storage 608. These instructions may be loaded into memory 606 for execution by processor unit 604. The processes of the different embodiments may be performed by processor unit 604 using computer implemented instructions, which may be located in a memory, such as memory 606.

These instructions are referred to as program code, computer usable program code, or computer readable program code that may be read and executed by a processor in processor unit 604. The program code, in the different embodiments, may be embodied on different physical or computer readable storage media, such as memory 606 or persistent storage 608.

Program code 618 is located in a functional form on computer readable media 620 that is selectively removable and may be loaded onto or transferred to data processing system 600 for execution by processor unit 604. Program code 618 and computer readable media 620 form computer program product 622. In one example, computer readable media 620 may be computer readable storage media 624 or computer readable signal media 626.

Computer readable storage media 624 may include, for example, an optical or magnetic disk that is inserted or placed into a drive or other device that is part of persistent storage 608 for transfer onto a storage device, such as a hard drive, that is part of persistent storage 608. Computer readable storage media 624 also may take the form of a persistent storage, such as a hard drive, a thumb drive, or a flash memory that is connected to data processing system 600. In some instances, computer readable storage media 624 may not be removable from data processing system 600.

Alternatively, program code 618 may be transferred to data processing system 600 using computer readable signal media 626. Computer readable signal media 626 may be, for example, a propagated data signal containing program code 618. For example, computer readable signal media 626 may be an electromagnetic signal, an optical signal, and/or any other suitable type of signal. These signals may be transmitted over communication links, such as wireless communication links, an optical fiber cable, a coaxial cable, a wire, and/or any other suitable type of communication link. In other words, the communication link and/or the connection may be physical or wireless in the illustrative examples.

In some illustrative embodiments, program code 618 may be downloaded over a network to persistent storage 608 from another device or data processing system through computer readable signal media 626 for use within data processing system 600. For instance, program code stored in a computer readable storage media in a server data processing system may be downloaded over a network from the server to data processing system 600. The data processing system providing program code 618 may be a server computer, a client computer, or some other device capable of storing and transmitting program code 618.

The different components illustrated for data processing system 600 are not meant to provide architectural limitations to the manner in which different embodiments may be implemented. The different advantageous embodiments may be implemented in a data processing system including components in addition to, or in place of, those illustrated for data processing system 600. Other components shown in FIG. 6 can be varied from the illustrative examples shown. The different embodiments may be implemented using any hardware device or system capable of executing program code. As one example, data processing system 600 may include organic components integrated with inorganic components and/or may be comprised entirely of organic components excluding a human being. For example, a storage device may be comprised of an organic semiconductor.

As another example, a storage device in data processing system 600 is any hardware apparatus that may store data. Memory 606, persistent storage 608, and computer readable media 620 are examples of storage devices in a tangible form.

In another example, a bus system may be used to implement communications fabric 602 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 606 or a cache, such as found in an interface and memory controller hub that may be present in communications fabric 602.

Figure 7:
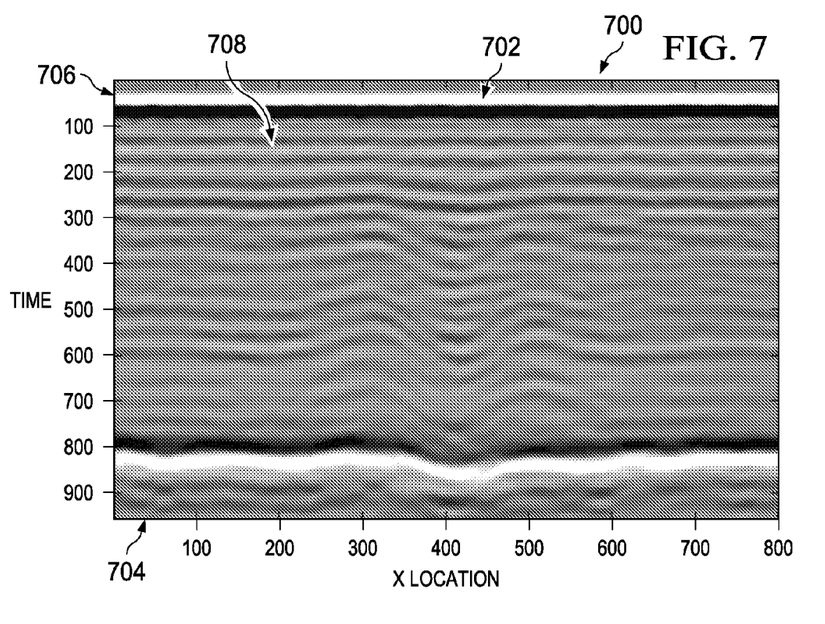
FIG. 7 is an illustration of an image in accordance with an advantageous embodiment.

With reference now to FIG. 7, an illustration of an image is depicted in accordance with an advantageous embodiment. In this illustrative example, image 700 is an example of one implementation for image 456 in FIG. 4. Image 700 is B-scan image 702 in this example.

In this depicted example, B-scan image 702 is an image that is generated using an ultrasonic measurement system. In particular, signals are sent into an object, such as a composite component, comprising a number of layers of composite material and having a particular depth. The signals are sent into the object at a plurality of locations that are identified with respect to a first coordinate location and a second coordinate location. The first coordinate location is an X location. The second coordinate location is a Y location.

The ultrasonic measurement system receives response signals in response to the signals sent into the composite component. B-scan image 702 is generated to present the amplitudes of the response signals received with respect to time and location. In particular, B-scan image 702 is generated for a particular Y location. Further, B-scan image 702 is generated with respect to X location 704 and time 706 for the particular Y location.

As illustrated, B-scan image 702 presents the amplitudes of the response signals received with respect to time and location. In particular, B-scan image 702 presents intensities 708 of the response signals.

Figure 8:
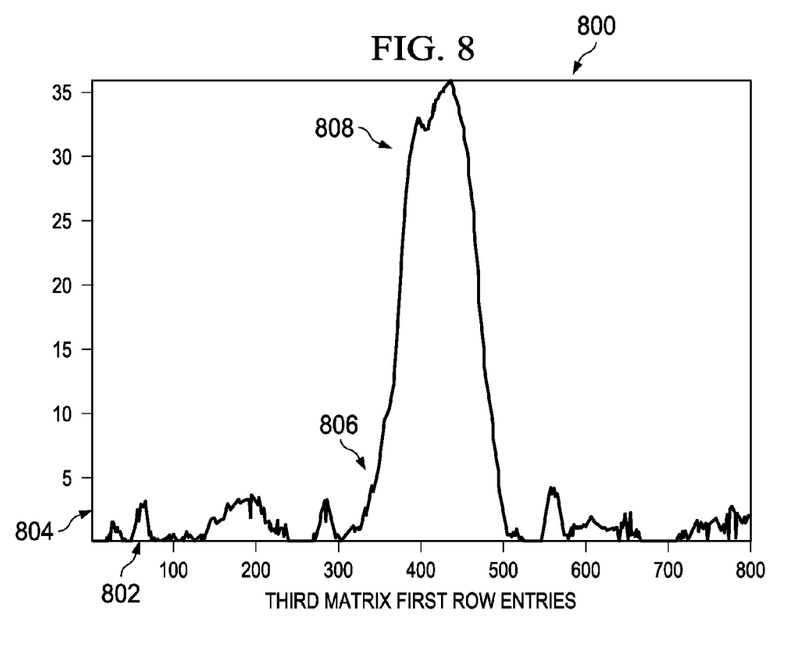
FIG. 8 is an illustration of a graph of a set of weighting factors in accordance with an advantageous embodiment.

With respect to FIG. 8, an illustration of a graph of a set of weight factors is depicted in accordance with an advantageous embodiment. In this illustrative example, graph 800 has horizontal axis 802 and vertical axis 804. Horizontal axis 802 is the entries in a particular row in a third matrix, such as third matrix 522 in FIG. 5. Additionally, the values for horizontal axis 802 may also be referred to as the indices for the rows in the third matrix. Vertical axis 804 is values of weighting factors.

As depicted, curve 806 identifies the values for the weighting factors in each entry in the particular row. Peak 808 in curve 806 indicates that an inconsistency may be present between the locations corresponding to about entry 350 and about entry 500 on the particular row for horizontal axis 802. Using curve 806, the width of the inconsistency may also be identified.

Figure 9:
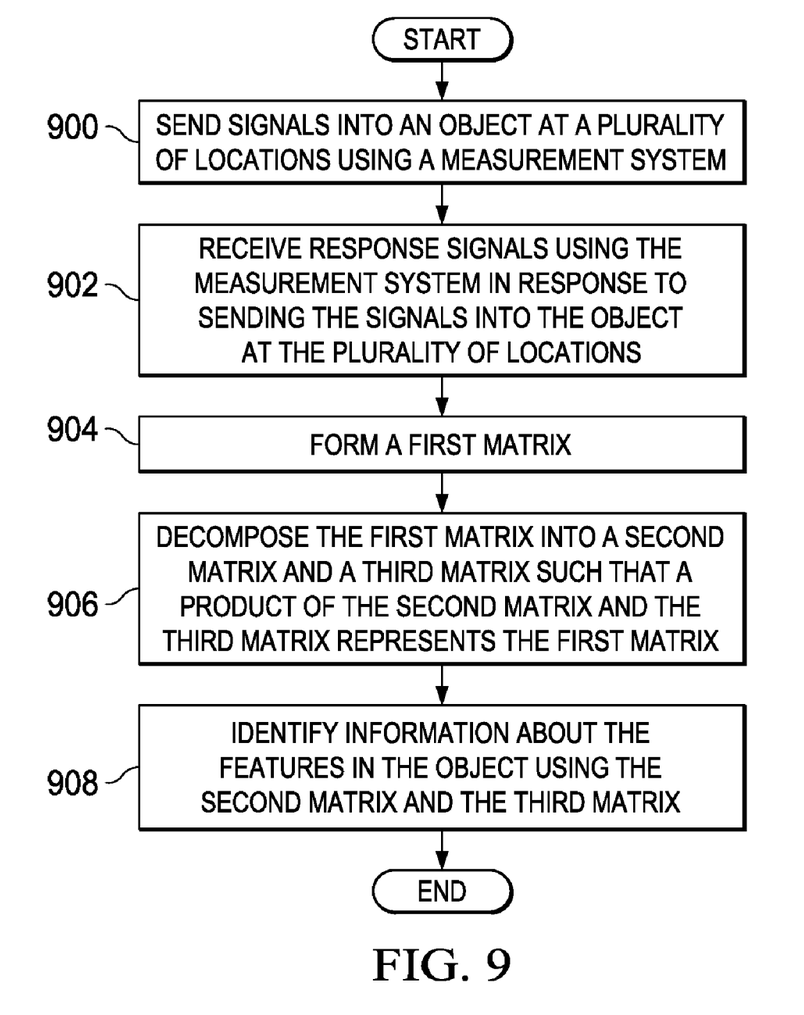
FIG. 9 is an illustration of a flowchart of a process for identifying features in an object in accordance with an advantageous embodiment.

With reference now to FIG. 9, an illustration of a flowchart of a process for identifying features in an object is depicted in accordance with an advantageous embodiment. The process illustrated in FIG. 9 may be implemented using testing system 430 in FIG. 4 to identify number of features 410 for object 404 in FIG. 4.

The process begins by sending signals into an object at a plurality of locations using a measurement system (operation 900). The measurement system takes the form of, for example, an ultrasonic measurement system, such as ultrasonic measurement system 436 in FIG. 4. The signals sent into the object in operation 900 are ultrasonic signals. The object may be, for example, a structure, a part, a component, a composite component, or some other suitable type of object. In this illustrative example, the object is a composite component.

Next, the process receives response signals at the plurality of locations in response to sending the signals into the object at the plurality of locations using the measurement system (operation 902). Thereafter, the process forms a first matrix (operation 904). Operation 904 may be performed using, for example, detection process 454 in FIG. 4. The first matrix takes the form of, for example, first matrix 504 in FIG. 5.

In this illustrative example, each entry in the first matrix contains an amplitude of a response signal in the response signals for a location in the plurality of locations where the response signal was received and a time at which the response signal was received with respect to when a corresponding signal in the signals was sent into the object. The time corresponds to a depth of the object in this example.

The process then decomposes the first matrix into a second matrix and a third matrix such that a product of the second matrix and the third matrix represents the first matrix (operation 906). Operation 906 may be performed using, for example, decomposition process 458 in detection process 454 in FIG. 4. Further, operation 906 may be performed using decomposition process 500 in FIG. 5. The decomposition performed in operation 906 may be a non-negative matrix factorization process.

In this depicted example, a number of columns in the second matrix corresponds to a number of features for the object. A number of rows in the third matrix corresponds to a number of sets of weighting factors for the number of features. Further, each entry in a row in the number of rows in the third matrix corresponds to a column in the first matrix in which each column in the first matrix is for a corresponding location in the plurality of locations.

Thereafter, the process identifies information about the features in the object using the second matrix and the third matrix (operation 908), with the process terminating thereafter. The information identified in operation 908 may be, for example, a number of dimensions for the features in the object.

As one illustrative example, in operation 908, a width of an inconsistency, such as a wrinkle, in a composite component may be identified. The width may be identified using a set of weighting factors in a row of the third matrix corresponding to the wrinkle. In this manner, the values for the weighting factors in the third matrix may be used to identify information for the features identified in the second matrix.

Figure 10:
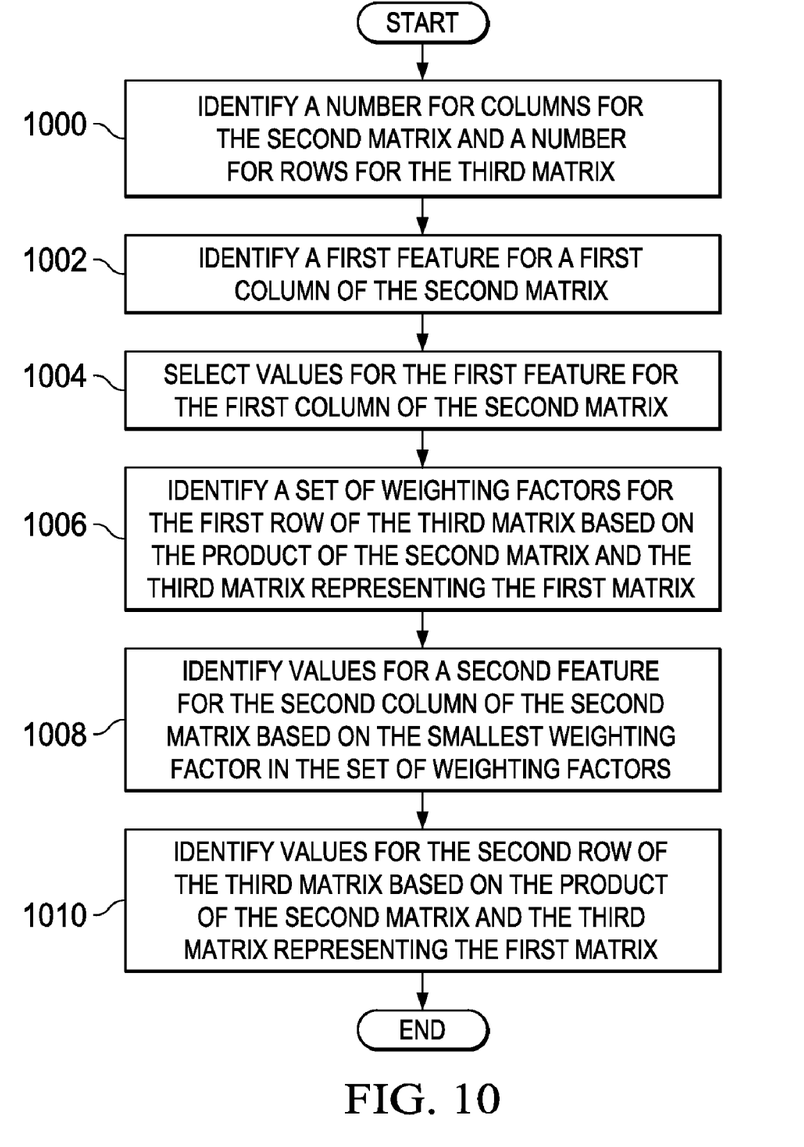
FIG. 10 is an illustration of a flowchart of a process for decomposing a first matrix into a second matrix and a third matrix in accordance with an advantageous embodiment.

With reference now to FIG. 10, an illustration of a flowchart of a process for decomposing a first matrix into a second matrix and a third matrix is depicted in accordance with an advantageous embodiment. The process illustrated in FIG. 10 is a more detailed process of operation 906 in FIG. 9. This process may be implemented using, for example, decomposition process 458 in FIG. 4. In particular, this process may be implemented using decomposition process 500 in FIG. 5.

The process begins by identifying a number for columns for the second matrix and a number for rows for the third matrix (operation 1000). The number identified for the columns is the same number as the number identified for the rows in this illustrative example. Further, this number is selected as two in this example. In other words, the second matrix is selected to have two columns, and the third matrix is selected to have two columns.

The process then identifies a first feature for a first column of the second matrix (operation 1002). The first feature may be identified through user input. In some illustrative examples, the decomposition process identifies the first feature. The first feature, in this illustrative example, is a number of layers of composite material being substantially parallel to a plane.

Next, the process selects values for the first feature for the first column of the second matrix (operation 1004). In operation 1004, these values may be selected as, for example, the values in the first column for the first matrix. In some illustrative examples, these values may be selected from a model of a part having the first feature for the number of layers of composite material for the part.

Next, the process identifies a set of weighting factors for the first row of the third matrix based on the product of the second matrix and the third matrix representing the first matrix (operation 1006).

By setting the first term to be substantially equal to the first matrix, the values for the first row of the third matrix may be identified. These values form the set of weighting factors for the first row of the third matrix. These weighting factors and the corresponding first column in the second matrix may be scaled such that the weighting factors are within a selected range of values, such as, for example, between zero and one.

The product of the first column of the second matrix and the first row of the third matrix containing the set of weighting factors represents the first matrix with respect to the first feature.

Thereafter, the process identifies values for a second feature for the second column of the second matrix based on the smallest weighting factor in the set of weighting factors (operation 1008). In operation 1008, the process uses the index of the entry containing the smallest weighting factor in the first row of the third matrix to identify the values in a corresponding column in the first matrix as the values for the second feature. For example, if the smallest weighting factor is in the eighth entry of the first row of the third matrix, the process identifies the values in the eighth column of the first matrix as the values for the second feature.

Next, the process identifies values for the second row of the third matrix based on the product of the second matrix and the third matrix representing the first matrix (operation 1010), with the process terminating thereafter. Operation 1010 is performed in a manner similar to operation 1006 as described above.

The product of the second column of the second matrix and the second row of the third matrix containing the set of weighting factors represents the first matrix with respect to the second feature.

In this manner, entries are identified for both the second matrix and the third matrix. The product of the second matrix and the third matrix represents the first matrix.

The flowcharts and block diagrams in the different depicted embodiments illustrate the architecture, functionality, and operation of some possible implementations of apparatus and methods in different advantageous embodiments. In this regard, each block in the flowcharts or block diagrams may represent a module, segment, function, and/or a portion of an operation or step. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved. Also, other blocks may be added in addition to the illustrated blocks in a flowchart or block diagram.

Thus, the different advantageous embodiments provide a method and apparatus for identifying features in an object. In one advantageous embodiment, signals are sent into the object at a plurality of locations using a measurement system. Response signals are received at the plurality of locations in response to sending the signals. A first matrix is formed in which each entry in the first matrix contains an amplitude of a response signal in the response signals for a location in the plurality of locations where the response signal was received and for a time at which the response signal was received with respect to when a corresponding signal in the signals was sent into the object.

The different advantageous embodiments can take the form of an entirely hardware embodiment, an entirely software embodiment, or an embodiment containing both hardware and software elements. Some embodiments are implemented in software, which includes, but is not limited to, forms, such as, for example, firmware, resident software, and microcode.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible apparatus that can contain, store, communicate, propagate, or transport the program for use by or in connection with the instruction execution system, apparatus, or device.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different advantageous embodiments has been presented for purposes of illustration and description and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for identifying features for an object, the method comprising:
    sending signals into the object at a plurality of locations using a measurement system;
    receiving response signals using the measurement system in response to sending the signals into the object at the plurality of locations;
    forming a first matrix in which each entry in the first matrix contains an amplitude of a response signal in the response signals for a location in the plurality of locations where the response signal was received and a time at which the response signal was received with respect to when a corresponding signal in the signals was sent into the object;
    decomposing the first matrix into a second matrix and a third matrix such that a product of the second matrix and the third matrix represents the first matrix, wherein a number of columns in the second matrix corresponds to a number of features for the object and wherein a number of rows in the third matrix corresponds to a number of sets of weighting factors for the number of features; and
    identifying information about the features in the object using the second matrix and the third matrix.

2. The method of claim 1, wherein entries in the first matrix, the second matrix, and the third matrix are non-negative.

3. The method of claim 1, wherein the decomposing step is performed using a non-negative matrix factorization process.

4. The method of claim 1, wherein the step of identifying the information about the features in the object using the second matrix and the third matrix comprises:
    determining whether an undesired inconsistency is present in the object using the second matrix and the third matrix in which the undesired inconsistency is a feature for the object; and
    identifying a number of dimensions for the undesired inconsistency in the object using entries in the third matrix.

5. The method of claim 1, wherein each entry in a row in the number of rows in the third matrix corresponds to a column in the first matrix in which each column in the first matrix is for a corresponding location in the plurality of locations.

6. The method of claim 1, wherein a product of a column in the number of columns in the second matrix and an entry in a row in the number of rows in the third matrix represents a column in the first matrix corresponding to the entry in the row in the third matrix with respect to a feature corresponding to a column in the second matrix.

7. The method of claim 1, wherein a feature in the features is a number of layers for the object being substantially parallel to a plane.

8. The method of claim 1, wherein a feature in the features is an undesired inconsistency in the object selected from one of a number of layers that are not substantially parallel to a plane, a wrinkle in the number of layers, and a number of voids within a region.

9. The method of claim 1, wherein the object is a composite component comprising a number of layers.

10. The method of claim 1, wherein the measurement system is an ultrasonic measurement system.

11. The method of claim 1, wherein the object is a component for a platform selected from one of a mobile platform, a stationary platform, a land-based object, an aquatic-based object, a space-based object, an aircraft, a surface ship, a tank, a personnel carrier, a train, a spacecraft, a space station, a satellite, a submarine, an automobile, a power plant, a bridge, a dam, a manufacturing facility, and a building.

12. An apparatus comprising:
    a measurement system configured to send signals into an object at a plurality of locations and receive response signals in response to sending the signals into the object at the plurality of locations;
    a computer system configured to form a first matrix in which each entry in the first matrix contains an amplitude of a response signal in the response signals for a location in the plurality of locations where the response signal was received and a time at which the response signal was received with respect to when a corresponding signal in the signals was sent into the object; decompose the first matrix into a second matrix and a third matrix such that a product of the second matrix and the third matrix represents the first matrix, wherein a number of columns in the second matrix corresponds to a number of features for the object and wherein a number of rows in the third matrix corresponds to a number of sets of weighting factors for the number of features; and identify information about the features in the object using the second matrix and the third matrix.

13. The apparatus of claim 12, wherein entries in the first matrix, the second matrix, and the third matrix are non-negative.

14. The apparatus of claim 12, wherein the computer system is configured to decompose the first matrix into the second matrix and the third matrix using a non-negative matrix factorization process.

15. The apparatus of claim 12, wherein in being configured to identify the information about the features in the object using the second matrix and the third matrix, the computer system is configured to determine whether an undesired inconsistency is present in the object using the second matrix and the third matrix in which the undesired inconsistency is a feature for the object; and identify a number of dimensions for the undesired inconsistency in the object using entries in the third matrix.

16. The apparatus of claim 12, wherein each entry in a row in the number of rows in the third matrix corresponds to a column in the first matrix in which each column in the first matrix is for a corresponding location in the plurality of locations.

17. The apparatus of claim 12, wherein a product of a column in the number of columns in the second matrix and an entry in a row in the number of rows in the third matrix represents a column in the first matrix corresponding to an entry in the row in the third matrix with respect to a feature corresponding to the column in the second matrix.

18. The apparatus of claim 12, wherein a feature in the number of features is a number of layers for the object being substantially parallel to a plane.

19. The apparatus of claim 12, wherein a feature in the number of features is an undesired inconsistency in the object selected from one of a number of layers that are not substantially parallel to a plane, a wrinkle in the number of layers, and a number of voids within a region.

20. The apparatus of claim 12, wherein the object is a composite component comprising a number of layers.

21. The apparatus of claim 12, wherein the sending and receiving steps are performed using an ultrasonic measurement system.

22. The apparatus of claim 12, wherein the object is a component for a platform selected from one of a mobile platform, a stationary platform, a land-based object, an aquatic-based object, a space-based object, an aircraft, a surface ship, a tank, a personnel carrier, a train, a spacecraft, a space station, a satellite, a submarine, an automobile, a power plant, a bridge, a dam, a manufacturing facility, and a building.

* * * * *